(12) United States Patent
Kim et al.

(10) Patent No.: US 9,835,565 B2
(45) Date of Patent: Dec. 5, 2017

(54) INSPECTION DEVICE OF DISPLAY DEVICE AND INSPECTION METHOD OF DISPLAY DEVICE

(71) Applicant: Samsung Display Co., Ltd., Yongin-si, Gyeonggi-Do (KR)

(72) Inventors: Wal jun Kim, Hwaseong-si (KR); JoongYoung Ryu, Cheonan-si (KR); Seung-Young Baeck, Cheonan-si (KR); Changhyun Ryu, Cheonan-si (KR); Deok joo Lim, Asan-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 233 days.

(21) Appl. No.: 14/746,427

(22) Filed: Jun. 22, 2015

(65) Prior Publication Data

US 2016/0187262 A1 Jun. 30, 2016

(30) Foreign Application Priority Data

Dec. 29, 2014 (KR) ........................ 10-2014-0192097

(51) Int. Cl.
*G01J 4/00* (2006.01)
*G01N 21/88* (2006.01)
(Continued)

(52) U.S. Cl.
CPC ..... *G01N 21/8806* (2013.01); *G01N 21/8422* (2013.01); *G01N 21/95* (2013.01);
(Continued)

(58) Field of Classification Search
CPC .......... G01N 21/8806; G01N 21/8422; G01N 21/95; G01N 2021/8427; G01N 2021/8848; G01N 2021/0683
(Continued)

(56) References Cited

U.S. PATENT DOCUMENTS

| 7,372,062 B2 | 5/2008 | Tanaka |
| 2011/0058038 A1* | 3/2011 | Twede .................... H04N 5/332 348/148 |

(Continued)

FOREIGN PATENT DOCUMENTS

| JP | 2001-289917 A | 10/2001 |
| JP | 2007-057487 A | 3/2007 |

(Continued)

*Primary Examiner* — Hina F Ayub
(74) *Attorney, Agent, or Firm* — H.C. Park & Associates, PLC (57) ABSTRACT

An inspection device of a display device includes a first illumination unit providing a first incident light to the display device at a first incident angle, a second illumination unit providing a second incident light to the display device at a second incident angle, a third illumination unit providing a third incident light to the display device at a third incident angle, and a defect detector receiving at least one of a first reflection light obtained from the first incident light reflected by the display device at a first reflection angle, a second reflection light obtained from the second incident light reflected by the display device at a second reflection angle, and a third reflection light obtained from the third incident light reflected by the display device at a third reflection angle to detect defects of the display device.

18 Claims, 4 Drawing Sheets

(51) Int. Cl.
*G01N 21/95* (2006.01)
*G01N 21/84* (2006.01)

(52) U.S. Cl.
CPC .............. *G01N 2021/8427* (2013.01); *G01N 2021/8848* (2013.01); *G01N 2201/0683* (2013.01)

(58) Field of Classification Search
USPC .......................................................... 356/364
See application file for complete search history.

(56) References Cited

U.S. PATENT DOCUMENTS

| | | | |
|---|---|---|---|
| 2012/0069339 A1* | 3/2012 | Toyoda .............. | G01N 21/8806 356/432 |
| 2016/0119557 A1* | 4/2016 | Hunt ................... | H04N 5/2256 348/131 |

FOREIGN PATENT DOCUMENTS

| | | |
|---|---|---|
| JP | 2008-058207 A | 3/2008 |
| JP | 2008-058270 A | 3/2008 |
| JP | 2011-226939 A | 11/2011 |
| JP | 2013-036888 A | 2/2013 |
| KR | 10-2007-0009705 A | 1/2007 |
| KR | 10-2010-0021051 A | 2/2010 |
| KR | 10-2011-0004188 A | 1/2011 |

\* cited by examiner

INSPECTION DEVICE OF DISPLAY DEVICE AND INSPECTION METHOD OF DISPLAY DEVICE

CLAIM OF PRIORITY

This U.S. non-provisional patent application claims the priority of and all the benefits accruing under 35 U.S.C. §119 of Korean Patent Application No. 10-2014-0192097, filed on Dec. 29, 2014 in the Korean Intellectual Property Office (KIPO), the contents of which are hereby incorporated by reference in its entirety.

BACKGROUND OF THE INVENTION

Field of the Invention

The present disclosure relates to an inspection device of a display device and an inspection method of the display device. More particularly, the present disclosure relates to an inspection device of a display device including a protective film attached on a display panel and an inspection method of the display device.

Description of the Related Art

In recent years, various display devices which have a lightweight and a slim volume compared to a cathode ray tube, have been developed. As examples of the display devices, a liquid crystal display device, an electrowetting display device, and an electrophoretic display device are widely used. The display device is applied to various information processing devices, such as a television set, a monitor, a notebook computer, a mobile phone, etc., to display an image. The display device includes a display panel and a protective film formed on the display panel.

In general, a visual inspection is performed on the display device by an inspector in a production line for the display device to inspect defects of the display device. However, there is a difference in degree between the visual inspection's results due to the inspector, and it is difficult to distinguish defects of the display device from defects of the protective film and foreign substances on the display panel from foreign substance on the protective film. Accordingly, an inspection device and an inspection method of the display device have been actively researched.

SUMMARY OF THE INVENTION

The present disclosure provides an inspection device of a display device, which is capable of distinguishing defects of a display panel, defects of a protective film, foreign substances on the display panel, and foreign substances on the protective film from each other.

The present disclosure provides an inspection method of the display device.

Embodiments of the inventive concept provide an inspection device of a display device, which comprises a display panel and a protective film disposed on the display panel, including a first illumination unit, a second illumination unit, a third illumination unit, and a defect detector. The first illumination unit provides a first incident light to the display device at a first incident angle. The second illumination unit provides a second incident light to the display device at a second incident angle greater than the first incident angle. The third illumination unit provides a third incident light to the display device at a third incident angle greater than the second incident angle. The defect detector receives at least one of a first reflection light obtained from the first incident light reflected by the display device at a first reflection angle, a second reflection light obtained from the second incident light reflected by the display device at a second reflection angle, and a third reflection light obtained from the third incident light reflected by the display device at a third reflection angle to detect defects of the display device.

The first illumination unit includes a first light source and a first polarization plate. The first light source provides the first incident light to the display device. The first polarization plate is disposed between the first light source and the display device, and the first polarization plate is a linear polarization plate, a circular polarization plate, or an elliptical polarization plate.

The first illumination unit further includes a band pass filter. The band pass filter is disposed between the first light source and the display device.

The second illumination unit includes a second light source and a second polarization plate. The second light source provides the second incident light to the display device. The second polarization plate is disposed between the second light source and the display device, and the second polarization plate is a linear polarization plate, a circular polarization plate, or an elliptical polarization plate.

The third illumination unit includes a third light source and a third polarization plate. The third light source provides the third incident light to the display device. The third polarization plate is disposed between the third light source and the display device, and the third polarization plate is a linear polarization plate, a circular polarization plate, or an elliptical polarization plate.

The first illumination unit includes a first polarization plate, the second illumination unit includes a second polarization plate, and the third illumination unit includes a third polarization plate. The first polarization plate polarizes the same light components as the second polarization plate, and the first polarization plate polarizes light components different from the third polarization plate.

The defect detector includes a photographing unit and a controller. The photographing unit receives at least one of the first reflection light, the second reflection light, and the third reflection light to take a picture of the display device. The controller receives a display device image from the photographing unit to detect the defects of the display device.

The photographing unit includes a camera and a fourth polarization plate. The camera takes the picture of the display device. The fourth polarization plate is disposed between the camera and the display device.

The camera includes at least one of a charge coupled device camera and a complementary metal oxide semiconductor camera.

The fourth polarization plate is a linear polarization plate, a circular polarization plate, or an elliptical polarization plate.

The first illumination unit includes a first polarization plate. The second illumination unit includes a second polarization plate. The third illumination unit includes a third polarization plate. The photographing unit includes a fourth polarization plate. The first polarization plate polarizes the same light components as the second polarization plate. The third polarization plate polarizes the same light components as the fourth polarization plate, and the first polarization plate polarizes light components different from the third polarization plate.

The first incident angle is in a range from about 0° to about 5°, the second incident angle is in a range from about 10° to about 20°, and the third incident angle is in a range from about 30° to about 50°.

Embodiments of the inventive concept provide an inspection method of a display device, which includes a display panel and a protective film disposed on the display panel, including providing a first incident light to the display device at a first incident angle, providing a second incident light to the display device at a second incident angle greater than the first incident angle, providing a third incident light to the display device at a third incident angle greater than the second incident angle, and receiving at least one of a first reflection light obtained from the first incident light reflected by the display device at a first reflection angle, a second reflection light obtained from the second incident light reflected by the display device at a second reflection angle, and a third reflection light obtained from the third incident light reflected by the display device at a third reflection angle to detect defects of the display device.

The providing of the first incident light includes disposing a first light source to provide the first incident light and disposing a first polarization plate between the first light source and the display device.

The providing of the first incident light further includes disposing a band pass filter between the first light source and the display device.

The providing of the second incident light includes disposing a second light source to provide the second incident light and disposing a second polarization plate between the second light source and the display device.

The providing of the third incident light includes disposing a third light source to provide the third incident light and disposing a third polarization plate between the third light source and the display device.

The detecting of the defects of the display device includes receiving at least one of the first reflection light, the second reflection light, and the third reflection light to take a picture of the display device and to provide a display device image and receiving the display device image to detect the defects of the display device.

The providing of the display device image includes receiving the first reflection light to take the picture of the display device and to provide a first display device image, receiving the second reflection light to take the picture of the display device and to provide a second display device image, and receiving the third reflection light to take the picture of the display device and to provide a third display device image.

The providing of the display device image includes disposing a camera to take the picture of the display device and disposing a fourth polarizing plate between the camera and the display device.

According to the above, the defects of the display panel, the defects of the protective film, the foreign substances attached to the display panel, and the foreign substances attached to the protective film may be distinguished from each other.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings, in which like reference symbols indicate the same or similar components, wherein.

DETAILED DESCRIPTION OF THE INVENTION

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numbers refer to like elements throughout. As used herein, the term "and/or" includes any and all combinations of one or more of the associated listed items.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, the present invention will be explained in detail with reference to the accompanying drawings.

Figure 1:
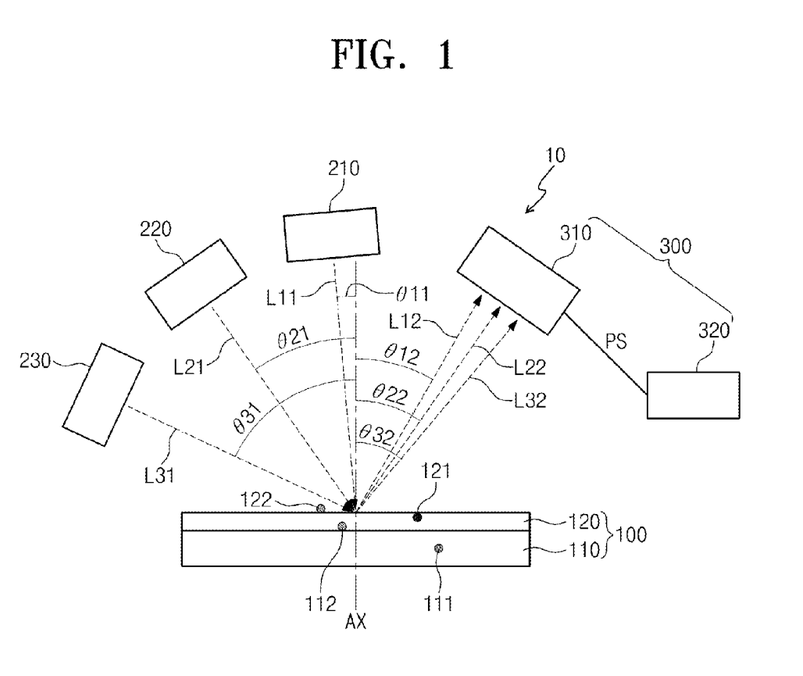
FIG. 1 is a view showing an inspection device of a display device according to an exemplary embodiment of the present disclosure.
Figure 2:
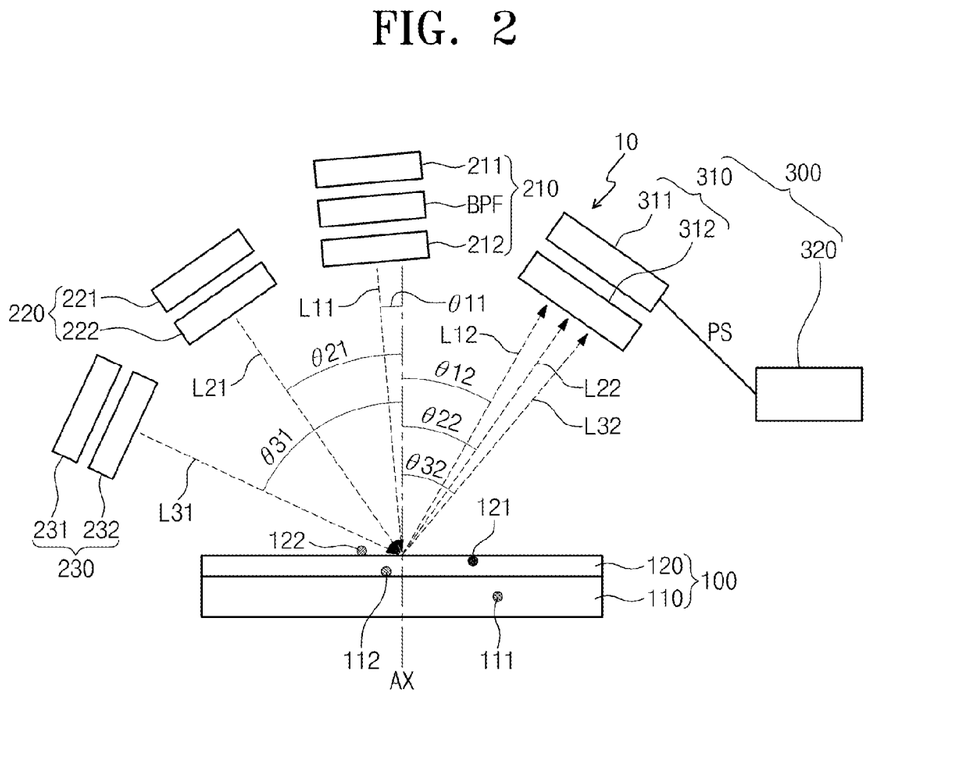
FIG. 2 is a view showing an inspection device of a display device according to an exemplary embodiment of the present disclosure.

FIG. 1 is a view showing an inspection device 10 of a display device 100 according to an exemplary embodiment of the present disclosure and FIG. 2 is a view showing an inspection device of a display device according to an exemplary embodiment of the present disclosure.

Referring to FIGS. 1 and 2, the inspection device 10 of the display device 100 includes a first illumination unit 210, a second illumination unit 220, a third illumination unit 230, and a defect detector 310.

The inspection device 10 of the display device 100 inspects defects, e.g., crack, scratch, etc., of the display device 100. The display device 100 includes a display panel 110 and a protective film 120 disposed on the display panel 110.

The display panel 110 is an organic light emitting display panel, a liquid crystal display panel, an electrophoretic display panel, or an electrowetting display panel, but it should not be limited to a specific display panel.

Defects 111, such as crack, scratch, etc., and foreign substances 112, e.g., dust, waste, etc., may exist on the display panel 110.

The protective film 120 is disposed on the display panel 110. The protective film 120 protects the display panel 110. The protective film 120 may have superior transparency, mechanical strength, heat-stability, moisture shielding property, and isotropic property. The protective film 120 is formed of at least one of triacetyl cellulose (TAC), discotic liquid crystal coating layer, VAC produced by Sumitomo, Kagaku Co., Ltd., cycloolefin polymer (COP), cycloolefin copolymer (COC), polycarbonate (PC), polyethylene terephthalate (PET), polypropylene (PP), polysulfone (PSF), and polymethylmethacrylate (PMMA).

The protective film 120 has an optical anisotropy. The protective film 120 retards a phase of a light. For instance, the protective film 120 has a polarization axis or a slow axis to retard the phase of the light vibrating along the polarization axis or the slow axis. The protective film 120 circularly polarizes a linearly-polarized light or linearly polarizes a circularly-polarized light, but it should not be limited thereto or thereby.

Defects 121, such as crack, scratch, etc., and foreign substances 122, e.g., dust, waste, etc., may exist on the protective film 120.

Figure 3A:
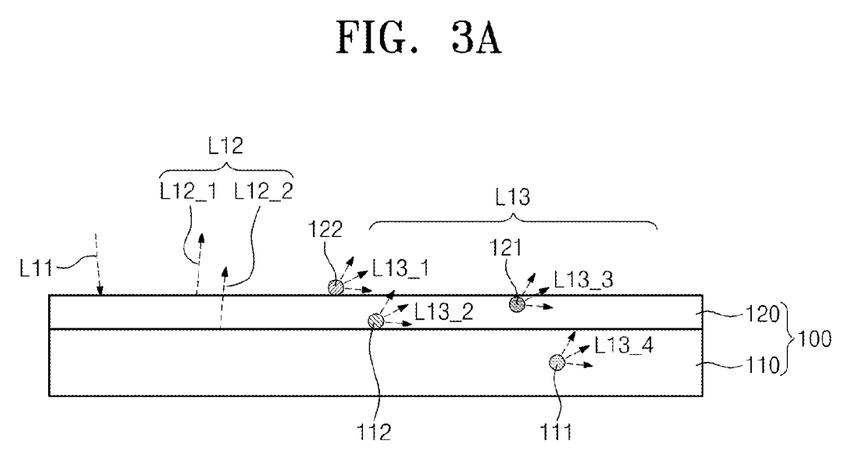
FIG. 3A is a cross-sectional view showing a first incident light, which is reflected and scattered after being provided to a display device from a first illumination unit included in an inspection device of a display device according to an exemplary embodiment of the present disclosure.

FIG. 3A is a cross-sectional view showing a first incident light L11, which is reflected and scattered after being provided to the display device 100 from the first illumination unit 210 included in the inspection device 10 of the display device 100 according to an exemplary embodiment of the present disclosure.

Referring to FIGS. 1, 2, and 3A, the first illumination unit 210 provides the first incident light L11 to the display device 100 at a first incident angle θ11. The first incident light L11 forms the first incident angle θ11 with a reference axis AX of the display device 100. The reference axis AX is substantially parallel to a thickness direction of the display panel 110. The first incident angle θ11 is in a range from about 0° to about 5°, but it should not be limited thereto or thereby.

When the first incident light L11 is provided to the display device 100, the first incident light L11 is reflected by the display device 100 at a first reflection angle θ12 to generate a first reflection light L12. The first reflection light L12 is provided to the defect detector 310. For the convenience of explanation, the first reflection angle θ12 is different from the first incident angle θ11 in FIG. 1, but the first reflection angle θ12 may be substantially the same as the first incident angle θ11 according to embodiments.

The first reflection light L12 includes a first protective reflection light L12_1 reflected from an upper surface of the protective film 120 and a first display reflection light L12_2 reflected from an upper surface of the display panel 110 after transmitting through the protective film 120. The first reflection light L12 includes lights reflected from areas of the display panel 110, in which the defects 111 and the foreign substances 112 do not exist, and lights reflected from areas of the protective film 120, in which the defects 121 and the foreign substances 122 do not exist.

When the first incident light L11 is provided to the display device 100, a first scattering light L13 is generated by the defects 111 existing on the display panel 110, the defects 121 existing on the protective film 120, the foreign substances 112 attached to the display panel 110, and the foreign substances 122 attached to the protective film 120. The first scattering light L13 is provided to the defect detector 310.

The first scattering light L13 includes a first protective foreign substance scattering light L13_1 scattered by the foreign substances 122 of the dust or the waste, which are attached to the protective film 120, a first display foreign substance scattering light L13_2 scattered by the foreign substances 112 of the dust or the waste, which are attached to the display panel 110, a first protective scattering light L13_3 scattered by the defects 121 existing on the protective film 120, and a first display scattering light L13_4 scattered by the defects 111 existing on the display panel 110.

The first illumination unit 210 includes a first light source 211 and a first polarization plate 212. The first light source 211 provides the light to the display device 100. The first polarization plate 212 is disposed between the first light source 211 and the display device 100. The first polarization plate 212 polarizes the light provided from the first light source 211. The first polarization plate 212 may be, but not limited to, a linear polarization plate, a circular polarization plate, or an elliptical polarization plate.

For instance, when the light provided from the first light source 211 is a light that is not polarized and the first polarization plate 212 is the circular polarization plate, the light provided from the first light source 211 is left-circularly polarized while transmitting through the first polarization plate 212. That is, the left-circularly polarized light is provided to the display device 100 at the first incident angle θ11 as the first incident light L11.

The first incident light L11 may be right-circularly polarized after being reflected by the upper surface of the protective film 120. Accordingly, each of the first protective reflection light L12_1 reflected by the upper surface of the protective film 120, the first protective foreign substance scattering light L13_1 scattered by the foreign substances 122 attached to the protective film 120, and the first protective scattering light L13_3 scattered by the defects 121 existing on the protective film 120 may be the right-circularly polarized light.

The first incident light L11 is linearly polarized in a horizontal direction while transmitting through the protective film 120 having the optical anisotropy, and the linearly-polarized light in the horizontal direction is linearly polarized in a vertical direction after being reflected by the upper surface of the display panel 110. The linearly-polarized light in the vertical direction is right-circularly polarized while transmitting through the protective film 120.

Therefore, each of the first display reflection light L12_2 reflected by the upper surface of the display panel 110, the first display foreign substance scattering light L13_2 scattered by the foreign substance 112 attached to the display panel 110, and the first display scattering light L13_4 scattered by the defects 111 existing on the display panel 110 may be the right-circularly polarized light.

Referring to FIG. 2, the first illumination unit 210 may further include a band pass filter BPF. The band pass filter BPF is disposed between the first light source 211 and the display device 100. FIG. 2 shows the band pass filter BPF disposed between the first light source 211 and the first polarization plate 212, but it should not be limited thereto or thereby. That is, the band pass filter BPF may be disposed between the first polarization plate 212 and the display device 100.

Figure 3B:
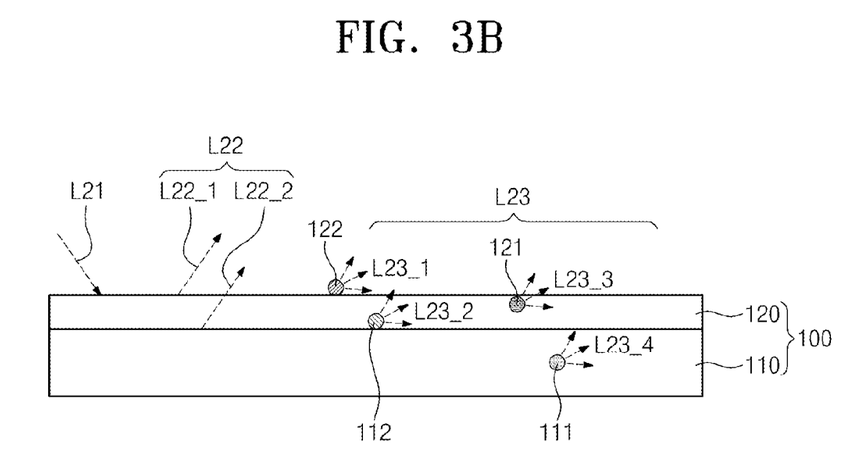
FIG. 3B is a cross-sectional view showing a second incident light, which is reflected and scattered after being provided to a display device from a second illumination unit included in an inspection device of a display device according to an exemplary embodiment of the present disclosure.

FIG. 3B is a cross-sectional view showing a second incident light L21, which is reflected and scattered after being provided to the display device 100 from the second illumination unit 220 included in the inspection device 10 of the display device 100 according to an exemplary embodiment of the present disclosure.

Referring to FIGS. 1, 2, and 3B, the second illumination unit 220 provides the second incident light L21 to the display device 100. The second incident light L21 forms a second incident angle θ21 with the reference axis AX of the display device 100. The reference axis AX is substantially parallel to the thickness direction of the display panel 110. The second incident angle θ21 is greater than the first incident angle θ11. The second incident angle θ21 is in a range from about 10° to about 20°, but it should not be limited thereto or thereby. When the second incident light L21 is provided to the display device 100, the second illumination unit 220 is disposed to have the second incident angle θ21 different from the first incident angle θ11, and thus the second illumination unit 220 may inspect defects that are not inspected by the first illumination unit 210.

When the second incident light L21 is provided to the display device 100, the second incident light L21 is reflected by the display device 100 at a second reflection angle θ22 to generate a second reflection light L22. The second reflection light L22 is provided to the defect detector 310. For the convenience of explanation, the second reflection angle θ22 is different from the second incident angle θ21 in FIG. 1, but the second reflection angle θ22 may be substantially the same as the second incident angle θ21 according to embodiments.

The second reflection light L22 includes a second protective reflection light L22_1 reflected from the upper surface of the protective film 120 and a second display reflection light L22_2 reflected from the upper surface of the display panel 110 after transmitting through the protective film 120. The second reflection light L22 includes lights reflected from areas of the display panel 110, in which the defects 111 and the foreign substances 112 do not exist, and lights reflected from areas of the protective film 120, in which the defects 121 and the foreign substances 122 do not exist.

When the second incident light L21 is provided to the display device 100, a second scattering light L23 is generated by the defects 111 existing on the display panel 110, the defects 121 existing on the protective film 120, the foreign substances 112 attached to the display panel 110, and the foreign substances 122 attached to the protective film 120. The second scattering light L23 is provided to the defect detector 310.

The second scattering light L23 includes a second protective foreign substance scattering light L23_1 scattered by the foreign substances 122 of the dust or the waste, which are attached to the protective film 120, a second display foreign substance scattering light L23_2 scattered by the foreign substances 112 of the dust or the waste, which are attached to the display panel 110, a second protective scattering light L23_3 scattered by the defects 121 existing on the protective film 120, and a second display scattering light L23_4 scattered by the defects 111 existing on the display panel 110.

The second illumination unit 220 includes a second light source 221 and a second polarization plate 222. The second light source 221 provides the light to the display device 100. The second polarization plate 222 is disposed between the second light source 221 and the display device 100. The second polarization plate 222 polarizes the light provided from the second light source 221. The second polarization plate 222 polarizes the same light components as the first polarization plate 212. The second polarization plate 222 may be, but not limited to, a linear polarization plate, a circular polarization plate, or an elliptical polarization plate.

For instance, when the light provided from the second light source 221 is a light that is not polarized and the second polarization plate 222 is the circular polarization plate, the light provided from the second light source 221 is left-circularly polarized while transmitting through the second polarization plate 222. That is, the left-circularly polarized light is provided to the display device 100 at the second incident angle θ21 as the second incident light L21.

The second incident light L21 may be right-circularly polarized after being reflected by the upper surface of the protective film 120. Accordingly, each of the second protective reflection light L22_1 reflected by the upper surface of the protective film 120, the second protective foreign substance scattering light L23_1 scattered by the foreign substances 122 attached to the protective film 120, and the second protective scattering light L23_3 scattered by the defects 121 existing on the protective film 120 may be the right-circularly polarized light.

The second incident light L21 is linearly polarized in the horizontal direction while transmitting through the protective film 120 having the optical anisotropy, and the linearly-polarized light in the horizontal direction is linearly polarized in a vertical direction after being reflected by the upper surface of the display panel 110. The linearly-polarized light in the vertical direction is right-circularly polarized while transmitting through the protective film 120.

Therefore, each of the second display reflection light L22_2 reflected by the upper surface of the display panel 110, the second display foreign substance scattering light L23_2 scattered by the foreign substance 112 attached to the display panel 110, and the second display scattering light L23_4 scattered by the defects 111 existing on the display panel 110 may be the right-circularly polarized light.

Figure 3C:
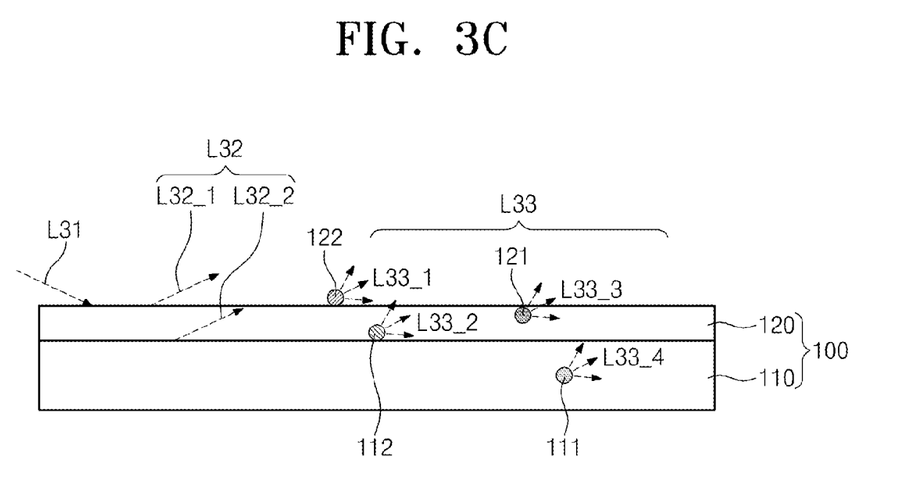
FIG. 3C is a cross-sectional view showing a third incident light, which is reflected and scattered after being provided to a display device from a third illumination unit included in an inspection device of a display device according to an exemplary embodiment of the present disclosure.

FIG. 3C is a cross-sectional view showing a third incident light L31, which is reflected and scattered after being provided to the display device 100 from the third illumination unit 230 included in the inspection device 10 of the display device 100 according to an exemplary embodiment of the present disclosure.

Referring to FIGS. 1, 2, and 3C, the third illumination unit 230 provides the third incident light L31 to the display device 100. The third incident light L31 forms a third incident angle θ31 with the reference axis AX of the display device 100. The reference axis AX is substantially parallel to the thickness direction of the display panel 110. The third incident angle θ31 is greater than each of the first and second incident angles θ11 and θ21. The third incident angle θ31 is in a range from about 30° to about 50°, but it should not be limited thereto or thereby.

When the third incident light L31 is provided to the display device 100, the third incident light L31 is reflected by the display device 100 at a third reflection angle θ32 to generate a third reflection light L32. The third reflection light L32 is provided to the defect detector 310. For the convenience of explanation, the third reflection angle θ32 is different from the third incident angle θ31 in FIG. 1, but the third reflection angle θ32 may be substantially the same as the third incident angle θ31 according to embodiments.

The third reflection light L32 includes a third protective reflection light L32_1 reflected from the upper surface of the protective film 120 and a third display reflection light L32_2 reflected from the upper surface of the display panel 110 after transmitting through the protective film 120. The third reflection light L32 includes lights reflected from areas of the display panel 110, in which the defects 111 and the foreign substances 112 do not exist, and lights reflected from areas of the protective film 120, in which the defects 121 and the foreign substances 122 do not exist.

When the third incident light L31 is provided to the display device 100, a third scattering light L33 is generated by the defects 111 existing on the display panel 110, the defects 121 existing on the protective film 120, the foreign substances 112 attached to the display panel 110, and the foreign substances 122 attached to the protective film 120. The third scattering light L33 is provided to the defect detector 310.

The third scattering light L33 includes a third protective foreign substance scattering light L33_1 scattered by the foreign substances 122 of the dust or the waste, which are attached to the protective film 120, a third display foreign substance scattering light L33_2 scattered by the foreign substances 112 of the dust or the waste, which are attached to the display panel 110, a third protective scattering light L33_3 scattered by the defects 121 existing on the protective film 120, and a third display scattering light L33_4 scattered by the defects 111 existing on the display panel 110.

The third illumination unit 230 is disposed to maximize the amount of the third protective foreign substance scattering light L33_1. The third illumination unit 230 includes a third light source 231 and a third polarization plate 232. The third light source 231 provides the light to the display device 100. The third polarization plate 232 is disposed between the third light source 231 and the display device 100. The third polarization plate 232 polarizes the light provided from the third light source 231. The third polarization plate 232 polarizes different light components from those of the first and second polarization plates 212 and 222. The third polarization plate 232 may be, but not limited to, a linear polarization plate, a circular polarization plate, or an elliptical polarization plate.

For instance, when the light provided from the third light source 231 is a light that is not polarized and the third polarization plate 232 is the linear polarization plate, the light provided from the third light source 231 is linearly polarized in the horizontal direction while transmitting through the third polarization plate 232. That is, the linearly-polarized light in the horizontal direction is provided to the display device 100 at the third incident angle θ31 as the third incident light L31.

The third incident light L31 may be linearly-polarized in the vertical direction after being reflected by the upper surface of the protective film 120. Accordingly, each of the third protective reflection light L32_1 reflected by the upper surface of the protective film 120, the third protective foreign substance scattering light L33_1 scattered by the foreign substances 122 attached to the protective film 120, and the third protective scattering light L33_3 scattered by the defects 121 existing on the protective film 120 may be the linearly-polarized light.

The third incident light L31 is left-circularly polarized while transmitting through the protective film 120 having the optical anisotropy, and the left-circularly polarized light is right-circularly polarized after being reflected by the upper surface of the display panel 110. The right-circularly polarized light is linearly polarized while transmitting through the protective film 120.

Therefore, each of the third display reflection light L32_2 reflected by the upper surface of the display panel 110, the third display foreign substance scattering light L33_2 scattered by the foreign substance 112 attached to the display panel 110, and the third display scattering light L33_4 scattered by the defects 111 existing on the display panel 110 may be the linearly-polarized light in the horizontal direction.

Referring to FIGS. 1, 2, and 3A to 3C, the defect detector 310 detects the defects of the display device 100. The defect detector 310 receives at least one of the first reflection light L12, the second reflection light L22, the third reflection light L32, the first scattering light L13, the second scattering light L23, and the third scattering light L33.

The defect detector 310 includes a photographing unit 310 and a controller 320. The photographing unit 310 takes a picture of the display device 100 and provides a display device image PS to the controller 320. The photographing unit 310 receives at least one of the first reflection light L12, the second reflection light L22, the third reflection light L32, the first scattering light L13, the second scattering light L23, and the third scattering light L33 to take the picture of the display device 100.

The photographing unit 310 receives at least one of the first reflection light L12 and the first scattering light L13 to take the picture of the display device 100 and provides a first display device image to the controller 320. The photographing unit 310 receives at least one of the second reflection light L22 and the second scattering light L23 to take the picture of the display device 100 and provides a second display device image to the controller 320. The photographing unit 310 receives at least one of the third reflection light L32 and the third scattering light L33 to take the picture of the display device 100 and provides a third display device image to the controller 320.

When the light is provided to the display panel 110 and the protective film 120, the light provided to defective areas, in which the defects and the foreign substances of the display panel 110 and the protective film 120 exist, is scattered and has a path different from that of the light provided to normal areas in which the defects and the foreign substances of the display panel 110 and the protective film 120 do not exist. Accordingly, when the photographing unit 310 takes the picture of the display device 100, the defective areas are distinguished from the normal areas. For instance, the display device image PS is distorted while being displayed in the defective areas.

The photographing unit 310 includes a camera 311 and a fourth polarization plate 312. The camera 311 takes the picture of the display device 100. The camera 311 includes at least one of a charge-coupled-device (CCD) camera and a complementary metal oxide semiconductor (CMOS) camera, but it should not be limited thereto or thereby.

The fourth polarization plate 312 is disposed between the camera 311 and the display device 100. The fourth polarization plate 312 polarizes at least one of the first reflection light L12, the second reflection light L22, the third reflection light L32, the first scattering light L13, the second scattering light L23, and the third scattering light L33. The fourth polarization plate 312 polarizes light components different from those polarized by the first and second polarization plates 212 and 222. The fourth polarization plate 312 polarizes the same light components as those polarized by the third polarization plate 232. The fourth polarization plate 312 may be, but not limited to, a linear polarization plate, a circular polarization plate, or an elliptical polarization plate.

The controller 320 receives the display device image PS from the photographing unit 310 to detect the defects of the display device 100. The controller 320 may distinguish the defects of the display panel 110, the defects of the protective film 120, the foreign substances attached to the display panel 110, and the foreign substances attached to the protective film 120 from each other.

The controller 320 compares the first, second, and third display device images provided from the photographing unit 310 to each other to distinguish the defects 111 existing on the display panel 110, the defects 121 existing on the protective film 120, the foreign substances, e.g., dust, waste, etc., attached to the upper surface of each of the display panel 110 and the protective film 120 from each other.

For instance, the areas, in which the defects 111 of the display panel 110, the defects 121 of the protective film 120, the foreign substances 112 attached to the display panel 110, and the foreign substance 122 attached to the protective film 120 exist, are distorted in the first display device image. The areas, in which the defects 111 of the display panel 110, the defects 121 of the protective film 120, the foreign substances 112 attached to the display panel 110, and the foreign substance 122 attached to the protective film 120 exist, are distorted in the second display device image. The areas, in which the defects 111 of the display panel 110, the defects 121 of the protective film 120, the foreign substances 112 attached to the display panel 110, and the foreign substances 122 attached to the protective film 120 exist, are distorted in the third display device image. As described above, since the third illumination unit 230 is disposed to allow the amount of the third protective scattering light L33_3 to be maximized, the areas, in which the foreign substances 122 attached to the protective film 120 exist, are brightly displayed in the third display device image.

Therefore, when each of the first and second display device images is compared to the third display device image, the areas in which the foreign substances 122 attached to the protective film 120 exist may be detected.

In each of the first and second display device images, the areas in which the defects 121 of the protective film 120 exist are brightest and the areas in which the defects 111 of the display panel 100 exist are darkest except for the areas in which the foreign substances 122 are attached to the protective film 120. In the case of the areas in which the defects 111 of the display panel 110 exist, the scattering light scattered by the defects 111 of the display panel 110 is provided to the photographing unit 310 after transmitting through the display panel 110 and the protective film 120, and thus light loss increases in the areas in which the defects 111 of the display panel 110 exist. As a result, the areas in which the defects 111 of the display panel 110 exist are relatively dark.

As described above, since the inspection device of the display device according to the present exemplary embodiment includes the first, second, and third illumination units, the inspection device may distinguish the defects of the display panel, the defects of the protective film, the foreign substances attached to the display panel, and the foreign substances attached to the protective film from each other even though the protective film is attached to the display panel.

Hereinafter, an inspection method of the display device according to an exemplary embodiment of the present disclosure will be described in detail.

Figure 4:
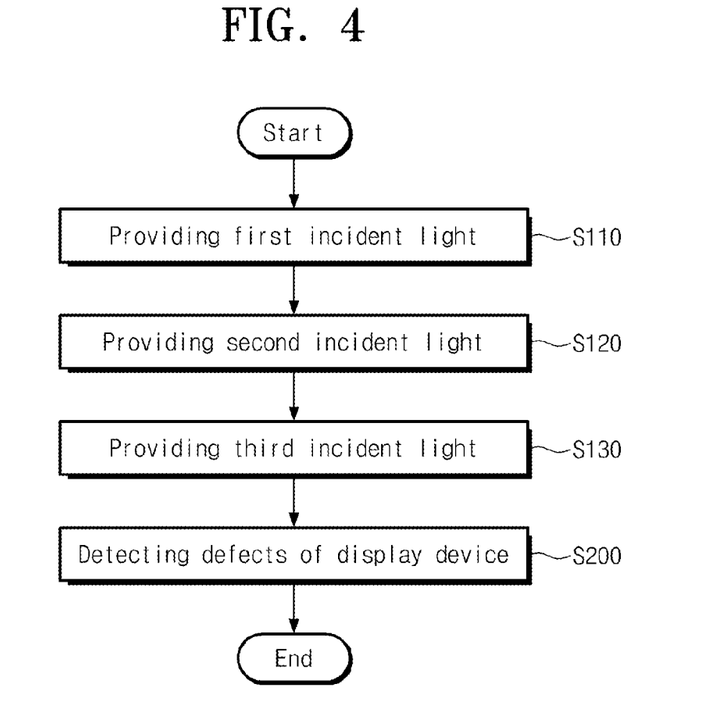
FIG. 4 is a flowchart showing an inspection method of a display device according to an exemplary embodiment of the present disclosure.

FIG. 4 is a flowchart showing the inspection method of the display device according to an exemplary embodiment of the present disclosure.

Referring to FIGS. 1, 2, 3A to 3C, and 4, the inspection method of the display device 100 includes providing the first incident light L11 to the display device 100 at the first incident angle θ11, which includes the display panel 110 and the protective film 120 disposed on the display panel 110 (S110), providing the second incident light L21 to the display device 100 at the second incident angle θ21 greater than the first incident angle θ11 (S120), providing the third incident light L31 to the display device 100 at the third incident angle θ31 greater than the second incident angle θ21 (S130), and receiving at least one of the first reflection light L12 obtained from the first incident light L11 reflected by the display device 100 at the first reflection angle θ12, the second reflection light L22 obtained from the second incident light L21 reflected by the display device 100 at the second reflection angle θ22, and the third reflection light L32 obtained from the third incident light L31 reflected by the display device 100 at the third reflection angle θ32 to detect the defects of the display device 100 (S200).

The providing of the first incident light L11 (S110), the providing of the second incident light L21 (S120), and the providing of the third incident light L31 (S130) are sequentially performed or randomly performed.

The providing of the first incident light L11 (S110) is performed by the first illumination unit 210. The first illumination unit 210 provides the first incident light L11 to the display device 100 at the first incident angle θ11. The first incident light L11 forms the first incident angle θ11 with the reference axis AX of the display device 100. The reference axis AX is substantially parallel to the thickness direction of the display panel 110. The first incident angle θ11 is in the range from about 0° to about 5°, but it should not be limited thereto or thereby.

When the first incident light L11 is provided to the display device 100, the first incident light L11 is reflected by the display device 100 at the first reflection angle θ12 to generate the first reflection light L12. The first reflection light L12 is provided to the defect detector 310.

The first reflection light L12 includes the first protective reflection light L12_1 reflected from the upper surface of the protective film 120 and the first display reflection light L12_2 reflected from the upper surface of the display panel 110 after transmitting through the protective film 120.

When the first incident light L11 is provided to the display device 100, the first scattering light L13 is generated by the defects 111 existing on the display panel 110, the defects 121 existing on the protective film 120, the foreign substances 112 attached to the display panel 110, and the foreign substances 122 attached to the protective film 120. The first scattering light L13 is provided to the defect detector 310.

The first scattering light L13 includes the first protective foreign substance scattering light L13_1 scattered by the foreign substances 122 of the dust or the waste, which are attached to the protective film 120, the first display foreign substance scattering light L13_2 scattered by the foreign substances 112 of the dust or the waste, which are attached to the display panel 110, the first protective scattering light L13_3 scattered by the defects 121 existing on the protective film 120, and the first display scattering light L13_4 scattered by the defects 111 existing on the display panel 110.

The providing of the first incident light L11 (S110) includes disposing the first light source 211 providing the light and disposing the first polarization plate 212 between the first light source 211 and the display device 100. The first light source 211 provides the light to the display device 100. The first polarization plate 212 is disposed between the first light source 211 and the display device 100. The first polarization plate 212 polarizes the light provided from the first light source 211. The first polarization plate 212 may be, but not limited to, the linear polarization plate, the circular polarization plate, or the elliptical polarization plate.

The providing of the first incident light L11 (S110) may further include disposing the band pass filter BPF between the first light source 211 and the display device 100. FIG. 2 shows the band pass filter BPF disposed between the first light source 211 and the first polarization plate 212, but it should not be limited thereto or thereby. That is, the band pass filter BPF may be disposed between the first polarization plate 212 and the display device 100.

The providing of the second incident light L21 (S120) is performed by the second illumination unit 220. The second illumination unit 220 provides the second incident light L21 to the display device 100 at the second incident angle θ21. The second incident light L21 forms the second incident angle θ21 with the reference axis AX of the display device 100. The reference axis AX is substantially parallel to the thickness direction of the display panel 110. The second incident angle θ21 is greater than the first incident angle θ11. The second incident angle θ21 is in the range from about 10° to about 20°, but it should not be limited thereto or thereby. When the second incident light L21 is provided to the display device 100, the second illumination unit 220 is disposed to have the second incident angle θ21 different from the first incident angle θ11, and thus the second illumination unit 220 may inspect defects that are not inspected by the first illumination unit 210.

When the second incident light L21 is provided to the display device 100, the second incident light L21 is reflected by the display device 100 at the second reflection angle θ22 to generate the second reflection light L22. The second reflection light L22 is provided to the defect detector 310.

The second reflection light L22 includes the second protective reflection light L22_1 reflected from the upper surface of the protective film 120 and the second display reflection light L22_2 reflected from the upper surface of the display panel 110 after transmitting through the protective film 120.

When the second incident light L21 is provided to the display device 100, the second scattering light L23 is generated by the defects 111 existing on the display panel 110, the defects 121 existing on the protective film 120, the foreign substances 112 attached to the display panel 110, and the foreign substances 122 attached to the protective film 120. The second scattering light L23 is provided to the defect detector 310.

The second scattering light L23 includes the second protective foreign substance scattering light L23_1 scattered by the foreign substances 122 of the dust or the waste, which are attached to the protective film 120, the second display foreign substance scattering light L23_2 scattered by the foreign substances 112 of the dust or the waste, which are attached to the display panel 110, the second protective scattering light L23_3 scattered by the defects 121 existing on the protective film 120, and the second display scattering light L23_4 scattered by the defects 111 existing on the display panel 110.

The providing of the second incident light L21 (S120) includes disposing the second light source 221 providing the light and disposing the second polarization plate 222 between the second light source 221 and the display device 100. The second light source 221 provides the light to the display device 100. The second polarization plate 222 is disposed between the second light source 221 and the display device 100. The second polarization plate 222 polarizes the light provided from the second light source 221. The second polarization plate 222 polarizes the same light components as those polarized by the first polarization plate 212. The second polarization plate 222 may be, but not limited to, the linear polarization plate, the circular polarization plate, or the elliptical polarization plate.

The providing of the third incident light L31 (S130) is performed by the third illumination unit 230. The third illumination unit 230 provides the third incident light L31 to the display device 100 at the third incident angle θ31. The third incident light L31 forms the third incident angle θ31 with the reference axis AX of the display device 100. The reference axis AX is substantially parallel to the thickness direction of the display panel 110. The third incident angle θ31 is greater than each of the first and second incident angles θ11 and θ21.

When the third incident light L31 is provided to the display device 100, the third incident light L31 is reflected by the display device 100 at the third reflection angle θ32 to generate the third reflection light L32. The third reflection light L32 is provided to the defect detector 310.

The third reflection light L32 includes the third protective reflection light L32_1 reflected from the upper surface of the protective film 120 and the third display reflection light L32_2 reflected from the upper surface of the display panel 110 after transmitting through the protective film 120.

When the third incident light L31 is provided to the display device 100, the third scattering light L33 is generated by the defects 111 existing on the display panel 110, the defects 121 existing on the protective film 120, the foreign substances 112 attached to the display panel 110, and the foreign substances 122 attached to the protective film 120. The third scattering light L33 is provided to the defect detector 310.

The third scattering light L33 includes the third protective foreign substance scattering light L33_1 scattered by the foreign substances 122 of the dust or the waste, which are attached to the protective film 120, the third display foreign substance scattering light L33_2 scattered by the foreign substances 112 of the dust or the waste, which are attached to the display panel 110, the third protective scattering light L33_3 scattered by the defects 121 existing on the protective film 120, and the third display scattering light L33_4 scattered by the defects 111 existing on the display panel 110. The third illumination unit 230 is disposed to allow the amount of the third protective foreign substance scattering light L33_1 to be maximized.

The providing of the third incident light L31 (S130) includes disposing the third light source 231 providing the light and disposing the third polarization plate 232 between the third light source 231 and the display device 100. The third light source 231 provides the light to the display device 100. The third polarization plate 232 is disposed between the third light source 231 and the display device 100. The third polarization plate 232 polarizes the light provided from the third light source 231. The third polarization plate 232 polarizes the light components different from those polarized by each of the first and second polarization plates 212 and 222. The third polarization plate 232 may be, but not limited to, the linear polarization plate, the circular polarization plate, or the elliptical polarization plate.

The detecting of the defects of the display device 100 (S200) includes receiving at least one of the first, second, and third reflection lights L12, L22, and L32 to take the picture of the display device 100 to provide the display device image PS and receiving the display device image PS to detect the defects of the display device 100.

The providing of the display device image PS includes receiving the first reflection light L12 to take the picture of the display device 100 and to provide the first display device image, receiving the second reflection light L22 to take the picture of the display device 100 and to provide the second display device image, and receiving the third reflection light L32 to take the picture of the display device 100 and to provide the third display device image.

The providing of the display device image PS includes disposing the camera 311 taking the picture of the display device 100 and disposing the fourth polarization plate 312 between the camera 311 and the display device 100.

The camera 311 takes the picture of the display device 100. The camera 311 includes at least one of the charge-coupled-device (CCD) camera and the complementary metal oxide semiconductor (CMOS) camera, but it should not be limited thereto or thereby.

The fourth polarization plate 312 is disposed between the camera 311 and the display device 100. The fourth polarization plate 312 polarizes at least one of the first reflection light L12, the second reflection light L22, the third reflection light L32, the first scattering light L13, the second scattering light L23, and the third scattering light L33. The fourth polarization plate 312 polarizes light components different from those polarized by the first and second polarization plates 212 and 222. The fourth polarization plate 312 polarizes the same light components as those polarized by the third polarization plate 232. The fourth polarization plate 312 may be, but not limited to, the linear polarization plate, the circular polarization plate, or the elliptical polarization plate.

The detecting of the defects of the display device 100 is performed by the controller 320. The controller 320 may distinguish the defects 111 of the display panel 110, the defects 121 of the protective film 120, the foreign substances 112 attached to the display panel 110, and the foreign substances 122 attached to the protective film 120 from each other.

The controller 320 compares the first, second, and third display device images to each other to distinguish the defects 111 existing on the display panel 110, the defects 121 existing on the protective film 120, the foreign substances attached to the upper surface of each of the display panel 110 and the protective film 120 from each other.

For instance, the areas, in which the defects 111 of the display panel 110, the defects 121 of the protective film 120, the foreign substances 112 attached to the display panel 110, and the foreign substance 122 attached to the protective film 120 exist, are distorted in the first display device image. The areas, in which the defects 111 of the display panel 110, the defects 121 of the protective film 120, the foreign substances 112 attached to the display panel 110, and the foreign substance 122 attached to the protective film 120 exist, are distorted in the second display device image. The areas, in which the defects 111 of the display panel 110, the defects 121 of the protective film 120, the foreign substances 112 attached to the display panel 110, and the foreign substances 122 attached to the protective film 120 exist, are distorted in the third display device image. As described above, since the third illumination unit 230 is disposed to allow the amount of the third protective scattering light L33_3 to be maximized, the areas, in which the foreign substances 122 attached to the protective film 120 exist, are brightly displayed in the third display device image.

Therefore, when each of the first and second display device images is compared to the third display device image, the areas in which the foreign substances 122 attached to the protective film 120 exist may be detected.

In each of the first and second display device images, the areas in which the defects 121 of the protective film 120 exist are brightest and the areas in which the defects 111 of the display panel 100 exist are darkest except for the areas in which the foreign substances 122 are attached to the protective film 120. In the case of the areas in which the defects 111 of the display panel 110 exist, the scattering light scattered by the defects 111 of the display panel 110 is provided to the photographing unit 310 after transmitting through the display panel 110 and the protective film 120, and thus a light loss in becomes increase in the areas in which the defects 111 of the display panel 110 exist. As a result, the areas in which the defects 111 of the display panel 110 exist are relatively dark.

As described above, since the inspection method of the display device according to the present exemplary embodiment includes the providing of the first incident light, the providing of the second incident light, and the providing of the third incident light, the defects of the display panel, the defects of the protective film, the foreign substances attached to the display panel, and the foreign substances attached to the protective film may be distinguished from each other even though the protective film is attached to the display panel.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:

1. An inspection device of a display device, which comprises a display panel and a protective film disposed on the display panel, comprising:
   a first illumination unit providing a first incident light to the display device at a first incident angle with respect to a normal to a surface of the display device;
   a second illumination unit providing a second incident light to the display device at a second incident angle with respect to the normal to the surface of the display device, the second incident angle being greater than the first incident angle;

a third illumination unit providing a third incident light to the display device at a third incident angle with respect to the normal to the surface of the display device, the third incident angle being greater than the second incident angle; and a defect detector receiving at least one of a first to a third reflection lights obtained from the first to a third incident lights reflected by the display device at different reflection angles, and a first to a third scattering lights obtained from the first to the third incident lights scattered by the display device to detect defects of the display device, wherein the defect detector comprises, a photographing unit taking a picture of the display device using received lights; and a controller receiving the pictures from the photographing unit to detect the defects of the display device, and the controller receives the pictures of the display device taken by i) a protective reflection light reflected from the upper surface of the protective film of each of the first to third reflection lights, ii) a protective foreign substance scattering light scattered by the foreign substances of the dust or the waste on the protective film, and iii) a protective scattering light scattered by the defects existing on the protective film of each of the first to third scattering lights, to distinguish defective areas and normal areas of the protective film, and the controller receives the pictures of the display device taken by i) a display reflection light reflected from the upper surface of the display panel of each of the first to third reflection lights, ii) a display foreign substance scattering light scattered by the foreign substances of the dust or the waste on the display panel, and iii) a display scattering light scattered by the defects existing on the display panel of each of the first to third scattering lights, to distinguish defective areas and normal areas of the display panel.

2. The inspection device of claim 1, wherein the first illumination unit comprises:

a first light source providing the first incident light to the display device; and a first polarization plate disposed between the first light source and the display device, and the first polarization plate is a linear polarization plate, a circular polarization plate, or an elliptical polarization plate.

3. The inspection device of claim 2, wherein the first illumination unit further comprises a band pass filter disposed between the first light source and the display device.

4. The inspection device of claim 1, wherein the second illumination unit comprises:

a second light source providing the second incident light to the display device; and a second polarization plate disposed between the second light source and the display device, and the second polarization plate is a linear polarization plate, a circular polarization plate, or an elliptical polarization plate.

5. The inspection device of claim 1, wherein the third illumination unit comprises:

a third light source providing the third incident light to the display device; and a third polarization plate disposed between the third light source and the display device, and the third polarization plate is a linear polarization plate, a circular polarization plate, or an elliptical polarization plate.

6. The inspection device of claim 1, wherein the first illumination unit comprises a first polarization plate, the second illumination unit comprises a second polarization plate, the third illumination unit comprises a third polarization plate, the first polarization plate polarizes the same light components as the second polarization plate, and the first polarization plate polarizes light components different from the third polarization plate.

7. The inspection device of claim 1, wherein the photographing unit comprises:

a camera taking the picture of the display device; and a fourth polarization plate disposed between the camera and the display device.

8. The inspection device of claim 7, wherein the camera comprises at least one of a charge coupled device camera and a complementary metal oxide semiconductor camera.

9. The inspection device of claim 7, wherein the fourth polarization plate is a linear polarization plate, a circular polarization plate, or an elliptical polarization plate.

10. The inspection device of claim 1, wherein the first illumination unit comprises a first polarization plate, the second illumination unit comprises a second polarization plate, the third illumination unit comprises a third polarization plate, the photographing unit comprises a fourth polarization plate, the first polarization plate polarizes the same light components as the second polarization plate, the third polarization plate polarizes the same light components as the fourth polarization plate, and the first polarization plate polarizes light components different from the third polarization plate.

11. The inspection device of claim 1, wherein the first incident angle is in a range from about 0° to about 5°, the second incident angle is in a range from about 10° to about 20°, and the third incident angle is in a range from about 30° to about 50°.

12. An inspection method of a display device that comprises a display panel and a protective film disposed on the display panel, comprising:

providing a first incident light to the display device at a first incident angle with respect to a normal to a surface of the display device;

providing a second incident light to the display device at a second incident angle with respect to the normal to the surface of the display device, the second incident angle being greater than the first incident angle;

providing a third incident light to the display device at a third incident angle with respect to the normal to the surface of the display device, the third incident angle being greater than the second incident angle;

providing an image of the display device using at least one of a first to a third reflection lights obtained from the first to the third incident lights reflected by the display device at different reflection angles, and a first to a third scattering lights obtained from the first to the third incident lights scattered by the display device;

distinguishing defective areas and normal areas of the protective film using i) a protective reflection light reflected from the upper surface of the protective film of each of the first to third reflection lights, ii) a protective foreign substance scattering light scattered by the foreign substances of the dust or the waste on the protective film, and iii) a protective scattering light scattered by the defects existing on the protective film of each of the first to third scattering lights; and distinguishing defective areas and normal areas of the display panel using i) a display reflection light reflected from the upper surface of the display panel of each of the first to third reflection lights, ii) a display foreign substance scattering light scattered by the foreign substances of the dust or the waste on the display panel, and iii) a display scattering light scattered by the defects existing on the display panel of each of the first to third scattering lights.

13. The inspection method of claim 12, wherein the providing of the first incident light comprises:
    disposing a first light source to provide the first incident light; and
    disposing a first polarization plate between the first light source and the display device.

14. The inspection method of claim 13, wherein the providing of the first incident light further comprises disposing a band pass filter between the first light source and the display device.

15. The inspection method of 12, wherein the providing of the second incident light comprises:
    disposing a second light source to provide the second incident light; and
    disposing a second polarization plate between the second light source and the display device.

16. The inspection method of claim 12, wherein the providing of the third incident light comprises:
    disposing a third light source to provide the third incident light; and
    disposing a third polarization plate between the third light source and the display device.

17. The inspection method of claim 12, wherein the providing of the display device image comprises:
    receiving the first reflection light to take the picture of the display device and to provide a first display device image;
    receiving the second reflection light to take the picture of the display device and to provide a second display device image; and
    receiving the third reflection light to take the picture of the display device and to provide a third display device image.

18. The inspection method of claim 12, wherein the providing of the display device image comprises:
    disposing a camera to take the picture of the display device; and
    disposing a fourth polarizing plate between the camera and the display device.

* * * * *